United States Patent
Macharia et al.

(10) Patent No.: US 8,103,385 B2
(45) Date of Patent: Jan. 24, 2012

(54) OPTIMIZING PRODUCT DRYING THROUGH PARALLEL LINES OF CENTRIFUGES AND DRYER PROCESS UNITS

(75) Inventors: Maina A. Macharia, Round Rock, TX (US); Donald Melvin Maxwell, Scottsdale, AZ (US); Srinivas Budaraju, Austin, TX (US)

(73) Assignee: Rockwell Automation Technologies, Inc., Mayfield Heights, OH (US)

( * ) Notice: Subject to any disclaimer, the term of this patent is extended or adjusted under 35 U.S.C. 154(b) by 559 days.

(21) Appl. No.: 12/242,568

(22) Filed: Sep. 30, 2008

(65) Prior Publication Data

US 2010/0082312 A1    Apr. 1, 2010

(51) Int. Cl.
G05D 11/00 (2006.01)
G05D 11/02 (2006.01)
G05B 21/00 (2006.01)
C12P 7/08 (2006.01)

(52) U.S. Cl. ........ 700/282; 700/273; 700/266; 435/161; 435/163

(58) Field of Classification Search ................ 700/282, 700/275, 90, 273, 266, 28; 73/1.36; 703/12; 435/255.2, 163

See application file for complete search history.

(56) References Cited

U.S. PATENT DOCUMENTS

| | | | |
|---|---|---|---|
| 3,379,421 A | | 4/1968 | Putman |
| 4,242,454 A | * | 12/1980 | Muller et al. ............... 435/162 |
| 4,374,198 A | * | 2/1983 | Miller et al. ............... 435/162 |
| 5,250,182 A | * | 10/1993 | Bento et al. ................ 210/641 |
| 5,662,810 A | * | 9/1997 | Willgohs ..................... 435/163 |
| 5,958,233 A | * | 9/1999 | Willgohs ................... 210/360.1 |
| 6,496,781 B1 | | 12/2002 | Chen et al. |
| 6,861,248 B2 | * | 3/2005 | Dale et al. ................. 435/255.2 |
| 7,070,967 B2 | * | 7/2006 | Dale et al. ................... 435/163 |
| 7,263,934 B2 | * | 9/2007 | Copeland et al. .............. 110/346 |
| 7,297,236 B1 | * | 11/2007 | Vander Griend .............. 435/161 |
| 7,404,262 B2 | * | 7/2008 | Jurkovich et al. .............. 34/381 |
| 7,572,353 B1 | * | 8/2009 | Vander Griend ................ 203/19 |

(Continued)

FOREIGN PATENT DOCUMENTS

EP    0303345 A2    2/1989

OTHER PUBLICATIONS

Aines G.; Klopfenstein, T.; and Stock, R., "MP51 Distillers Grains", 1986, Historical Materials from University of Nebraska-Lincoln Extension, obtained online Aug. 11, 2011 at www.extension.unl.edu/publications.*

(Continued)

*Primary Examiner* — Kakali Chaki
*Assistant Examiner* — Kelvin Booker
(74) *Attorney, Agent, or Firm* — Fletcher Yoder, PC; William R. Walbrun; John M. Miller

(57) ABSTRACT

The present invention provides novel techniques for controlling flow rates through parallel distribution paths of centrifuges and dryers using model predictive control. In particular, the present techniques are presented in the context of biofuel production, wherein control of whole stillage flow rates through parallel distribution paths of centrifuges and dryers may be optimized. However, the present techniques may also be applied to other suitable applications, such as the production of agricultural products, where parallel distribution paths of centrifuges and dryers may be used to separate solids from liquids as well as to remove water from the solids and liquids.

20 Claims, 5 Drawing Sheets

U.S. PATENT DOCUMENTS

| | | | |
|---|---|---|---|
| 7,572,627 B2 * | 8/2009 | Rieke et al. | 435/293.2 |
| 7,608,729 B2 * | 10/2009 | Winsness et al. | 554/9 |
| 7,666,637 B2 * | 2/2010 | Nguyen | 435/165 |
| 7,730,633 B2 * | 6/2010 | Jurkovich et al. | 34/381 |
| 7,829,680 B1 * | 11/2010 | Sander et al. | 530/412 |
| 7,831,318 B2 * | 11/2010 | Bartee et al. | 700/29 |
| 7,840,363 B2 * | 11/2010 | Stephenson et al. | 702/45 |
| 7,867,365 B2 * | 1/2011 | Brown | 203/19 |
| 7,931,784 B2 * | 4/2011 | Medoff | 204/157.63 |
| 7,932,065 B2 * | 4/2011 | Medoff | 435/165 |
| 7,933,849 B2 * | 4/2011 | Bartee et al. | 706/19 |
| 7,937,850 B2 * | 5/2011 | Tate et al. | 435/161 |
| 2003/0019736 A1 * | 1/2003 | Garman | 203/23 |
| 2004/0033457 A1 | 2/2004 | Zhang et al. | |
| 2004/0082044 A1 * | 4/2004 | Prevost et al. | 435/161 |
| 2004/0087808 A1 * | 5/2004 | Prevost et al. | 554/9 |
| 2006/0194296 A1 * | 8/2006 | Hammond et al. | 435/161 |
| 2007/0014905 A1 * | 1/2007 | Chen et al. | 426/490 |
| 2007/0036881 A1 * | 2/2007 | Griffith | 435/161 |
| 2007/0078530 A1 | 4/2007 | Blevins et al. | |
| 2007/0184541 A1 * | 8/2007 | Karl et al. | 435/161 |
| 2007/0254089 A1 * | 11/2007 | Hickey et al. | 426/624 |
| 2008/0026101 A1 * | 1/2008 | Nickel et al. | 426/52 |
| 2008/0028675 A1 | 2/2008 | Clifford et al. | |
| 2008/0103747 A1 * | 5/2008 | Macharia et al. | 703/11 |
| 2008/0103748 A1 * | 5/2008 | Axelrud et al. | 703/12 |
| 2008/0104003 A1 | 5/2008 | Macharia et al. | |
| 2008/0108048 A1 | 5/2008 | Bartee et al. | |
| 2008/0109100 A1 | 5/2008 | Macharia et al. | |
| 2008/0109200 A1 * | 5/2008 | Bartee et al. | 703/12 |
| 2008/0110577 A1 * | 5/2008 | Winsness | 159/5 |
| 2008/0153149 A1 * | 6/2008 | Van Leeuwen et al. | 435/254.1 |
| 2008/0167852 A1 * | 7/2008 | Bartee et al. | 703/11 |
| 2008/0176298 A1 * | 7/2008 | Randhava et al. | 435/134 |
| 2009/0004712 A1 * | 1/2009 | Rehkopf et al. | 435/161 |
| 2009/0031615 A1 * | 2/2009 | Joshi et al. | 44/307 |
| 2009/0047382 A1 * | 2/2009 | Cates et al. | 426/14 |
| 2009/0093027 A1 * | 4/2009 | Balan et al. | 435/165 |
| 2009/0117635 A1 * | 5/2009 | Bradley et al. | 435/165 |
| 2009/0148920 A1 * | 6/2009 | Schreck | 435/135 |
| 2009/0171129 A1 * | 7/2009 | Evanko et al. | 568/916 |
| 2009/0176289 A1 * | 7/2009 | Friedmann | 435/167 |
| 2009/0181153 A1 * | 7/2009 | Bendorf et al. | 435/93 |
| 2009/0227004 A1 * | 9/2009 | Dale | 435/271 |
| 2009/0240603 A1 * | 9/2009 | Stephenson et al. | 705/28 |
| 2009/0250412 A1 * | 10/2009 | Winsness et al. | 210/774 |
| 2009/0263540 A1 * | 10/2009 | Allen et al. | 426/11 |
| 2009/0286295 A1 * | 11/2009 | Medoff et al. | 435/161 |
| 2009/0326678 A1 * | 12/2009 | Stephenson et al. | 700/3 |
| 2009/0326695 A1 * | 12/2009 | Macharia et al. | 700/103 |
| 2010/0055741 A1 * | 3/2010 | Galvez et al. | 435/160 |
| 2010/0082139 A1 * | 4/2010 | Macharia et al. | 700/103 |
| 2010/0082140 A1 * | 4/2010 | Macharia et al. | 700/103 |
| 2010/0082166 A1 * | 4/2010 | Macharia et al. | 700/282 |
| 2010/0082312 A1 * | 4/2010 | Macharia et al. | 703/9 |
| 2010/0087687 A1 * | 4/2010 | Medoff | 435/155 |
| 2010/0124583 A1 * | 5/2010 | Medoff | 435/107 |
| 2010/0179315 A1 * | 7/2010 | Medoff | 536/123.13 |
| 2010/0196994 A1 * | 8/2010 | van Leeuwen et al. | 435/256.1 |
| 2010/0221804 A1 * | 9/2010 | Veit et al. | 435/165 |
| 2010/0304439 A1 * | 12/2010 | Medoff | 435/72 |
| 2010/0317091 A1 * | 12/2010 | Veit et al. | 435/286.1 |
| 2010/0331580 A1 * | 12/2010 | Ridgley | 568/840 |
| 2011/0027837 A1 * | 2/2011 | Medoff | 435/155 |
| 2011/0039317 A1 * | 2/2011 | Medoff | 435/155 |
| 2011/0108409 A1 * | 5/2011 | Brown | 203/42 |
| 2011/0173835 A1 * | 7/2011 | Tate et al. | 34/191 |

OTHER PUBLICATIONS

Arora, A.; Dien, B.S.; Belyea, R.L.; Wang, P.; Singh, V.; Tumbleson, M.E.; and Rausch, K.D., "Thin Stillage Fractionation Using Ultrafiltration: Resistance in Series Model", Feb. 2008, Bioprocess Biosyst Eng (2009) 32: 225-233.*

Budaraju, S.; Macharia, M.; and Kramer, D., "Plant-Wide Optimization of Sterling Ethanol LLC", Jun. 2008, Ethanol Producer Magazine, obtained online Aug. 11, 2011 at www.ethanolproducer.com.*

Galitsky, C.; Worrell, E.; and Ruth, M., Energy Efficiency Improvement and Cost Saving Opportunities for the Corn Wet Milling Industry—An Energy Star Guide for Energy and Plant Managers, Jul. 2003, Ernest Orlando Lawrence Berkeley National Laboratory, LBNL-52307.*

McAloon, A.; Taylor, F.; Yee, W.; Ibsen, K. and Wooley, R., "Determining the Cost of Producing Ethanol from Corn Starch and Lignocellulosic Feedstocks", Oct. 2000, National Renewable Energy Laboratory Technical Report—U.S. Department of Agriculture and U.S. Department of Energy, NREL/TP-580-28893.*

Monitor Technologies, LLC, "Ethanol Production Level Measurement Solutions", Jul. 2006, Monitor Technologies LLC, 44W320 Keslinger Rd, PO Box 8048, Elburn, IL 60119, obtained online Aug. 11, 2011 at www.monitortech.com.*

Tay, M., "Case Study: Reduce Energy Costs, Increase Production with Model Predict Control", Aug. 2007, Ethanol Producer Magazine, obtained online Aug. 11, 2011 at www.ethanolproducer.com.*

Tay, M. and Macharia, M., "Reducing Energy Costs with Model Predictive Control Solutions", Jul. 2006, Ethanol Producer Magazine, obtained online Aug. 11, 2011 at www.ethanolproducer.com.*

Wallace, R.; Ibsen, K.; McAloon, A. and Yee, W., "Feasibility Study for Co-Locating and Integrating Ethanol Production Plants from Corn Starch and Lignocellulosic Feedstocks", Sep. 2005, National Renewable Energy Laboratory—U.S. Department of Agriculture and U.S. Department of Energy, NREL/TP-510-37092, USDA-ARS 1935-41000-055-00D.*

U.S. Appl. No. 12/052,117, filed Mar. 20, 2008, Stephenson et al.
U.S. Appl. No. 12/052,159, filed Mar. 20, 2008, Stephenson et al.
U.S. Appl. No. 12/165,371, filed Jun. 30, 2008, Macharia et al.

* cited by examiner

OPTIMIZING PRODUCT DRYING THROUGH PARALLEL LINES OF CENTRIFUGES AND DRYER PROCESS UNITS

BACKGROUND

The present invention relates generally to control systems, and more particularly to model predictive control employing novel techniques for optimizing drying processes, such as the drying of biofuel stillage products between parallel paths.

Many processing plants, such as biofuel production plants, include separation and drying processes which may use centrifuges, dryers, evaporators, and so forth. These processes may separate solids from liquids as well as remove water from the solid and liquid products. As these plants expand, multiple parallel paths for the separation and drying processes may be used. This type of expansion may allow for increased throughput. In addition, this expansion may be integrated into the current plant to allow for flexibility in operating paths. This cross-integration in plant expansions is not uncommon as this provides the plant operating flexibility and the ability to shut sections of the plant down without shutting the entire plant down. However, when this type of expansion is implemented, plant operators may be presented with control issues regarding how to distribute flow rates through the parallel paths. In particular, the equipment in the parallel paths may not always be characterized by the same performance profiles and efficiencies. Therefore, simply routing proportional flow rates through the parallel paths (e.g., 20% flow rate through each of five parallel paths) may not be the most desirable control scheme.

BRIEF DESCRIPTION

The present invention provides novel techniques for controlling flow rates through parallel distribution paths of centrifuges and dryers using model predictive control. In particular, the present techniques are presented in the context of biofuel production, wherein control of whole stillage flow rates through parallel distribution paths of centrifuges and dryers may be optimized. However, the present techniques may also be applied to other suitable applications, such as the production of agricultural products, where parallel distribution paths of centrifuges and dryers may be used to separate solids from liquids as well as to remove water from the solids and liquids.

In general, the present techniques provide a method for controlling the distribution of stillage through centrifuges and dryers. The method includes determining operating variables of a plurality of centrifuges and dryers. The plurality of centrifuges and dryers are located within parallel distribution paths. The method also includes determining constraints of the plurality of centrifuges and dryers. The method further includes determining an overall optimization objective. In addition, the method includes determining optimal flow rates of stillage through the parallel distribution paths based upon the determined operating variables, constraints, and overall optimization objective. The method also includes controlling the flow rates of stillage between the parallel distribution paths based upon the optimal flow rate determinations.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
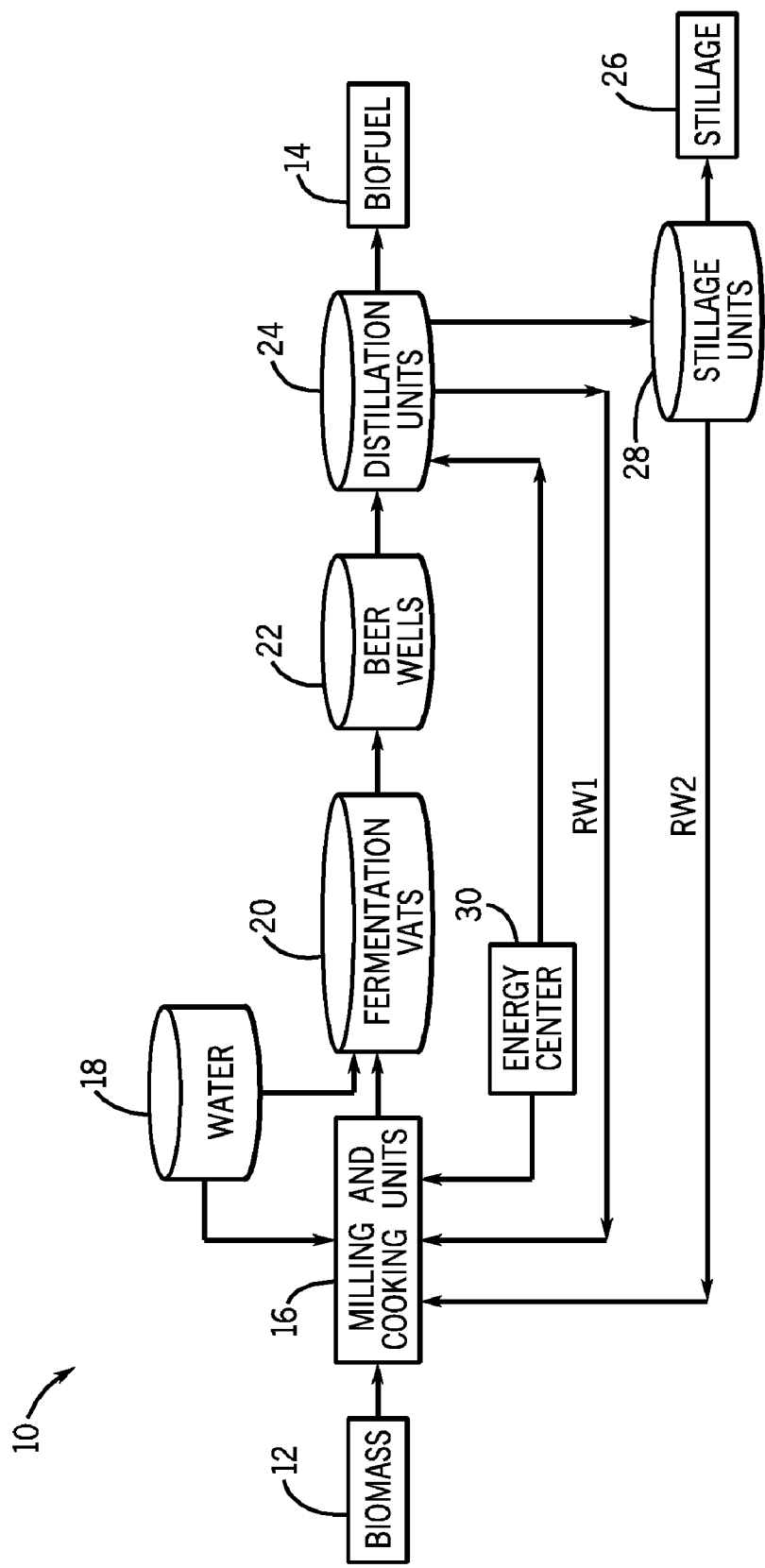
FIG. 1 is a diagram of an exemplary production plant.

Turning now to the drawings, FIG. 1 is a diagram of an exemplary biofuel production plant 10, illustrating how biomass 12 may be processed through several stages to produce biofuel 14. Biomass 12 may first be provided to a milling and cooking process, e.g., milling and cooking units 16, where water 18 (and possibly recycled water RW1 and RW2) may be added and the biomass 12 may be broken down to increase the surface area-to-volume ratio. This increase in surface area may allow for sufficient interaction of the water 18 and biomass 12 surface area to achieve a solution of fermentable sugars in water 18. The mixture, a biomass 12 and water 18 slurry, may be cooked to promote an increase in the amount of contact between the biomass 12 and water 18 in solution and to increase the separation of carbohydrate biomass from non-carbohydrate biomass. The output of the milling and cooking units 16 (i.e., the fermentation feed or mash) may then be sent to a fermentation process, where one or more fermentation vats 20 may operate to ferment the biomass/water mash produced by the milling and cooking units 16.

The fermentation process may require additional water 18 to control the consistency of material to the fermentation vats 20 (also referred to herein as a fermenter or fermentation tank). Biomass 12 may be converted by yeast and enzymes into a biofuel 14 and by-products such as carbon dioxide, water and non-fermentable biomass (solids), in the fermentation vats 20. The fermentation process is a batch process and may include multiple fermenters operating in parallel. The batch start times may be staggered in order to optimize the utilization of the capacity of the beer wells 22 and smoothly distribute the flow of fermentation feed to the fermentation process and the flow of biofuel 14 and stillage as output from the fermentation process.

After being temporarily stored in the beer wells 22, the output from the fermentation vats 20 may be sent to a distillation process, e.g., one or more distillation units 24, to separate biofuel 14 from water 18, carbon dioxide, and non-fermentable solids. If the biofuel 14 has to be dehydrated to moisture levels less than 5% by volume, the biofuel 14 may be processed through a processing unit called a molecular sieve or similar processing units (not shown). The finalized biofuel 14 may then be processed to ensure it is denatured and not used for human-consumption.

The distillation units 24 may separate the biofuel 14 from water 18. Water 18 may be used in the form of steam for heat and separation, and the condensed water may be recycled (RW1) back to the milling and cooking units 16. Stillage 26 (non-fermentable solids and yeast residue), the heaviest output of the distillation units 24, may be sent to stillage processing units 28 for further development of co-products from the biofuel 14 production process.

The stillage processing units 28 may separate additional water from the cake solids and recycle the water (RW2) back to the milling and cooking units 16. Several stillage processing options may be utilized, including: (1) selling the stillage with minimal processing and (2) further processing the stillage by separating moisture from the solid products via one or more centrifuge units (not shown). Using the centrifuge units, the non-fermentable solids may be transported to dryers (not shown) for further moisture removal. A portion of the stillage liquid (concentrate) may also be recycled back to the fermentation vats 20. However, the bulk of the flow may generally be sent to evaporator units (not shown), where more liquid may be separated from the liquid stream, causing the liquid stream to concentrate into syrup, while solid stillage may be sent to a drying process, e.g., using a drying unit or evaporator, to dry the solid stillage to a specified water content. The syrup may then be sent to a syrup tank (not shown). Syrup in inventory may be processed using a number of options. For instance, the syrup may be: (1) sprayed in dryers to achieve a specified color or moisture content, (2) added to the partially dried stillage product, or (3) sold as a separate liquid product. The evaporator units may have a water by-product stream that is recycled back to the milling and cooking units 16.

An energy center 30 may supply energy to many of the processing units, e.g., the milling and cooking units 16, the distillation units 24 and mole-sieve units, and the stillage processing units 28. The energy center 30 may constitute a thermal oxidizer unit and heat recovery steam generator (HRSG) that may destroy volatile organic compounds (VOCs) and provide steam to the evaporators, distillation units 24, cooking system units (e.g., in 16), and dehydration units. The energy center 30 may typically be the largest source of heat in a biofuel plant 10.

Figure 2:
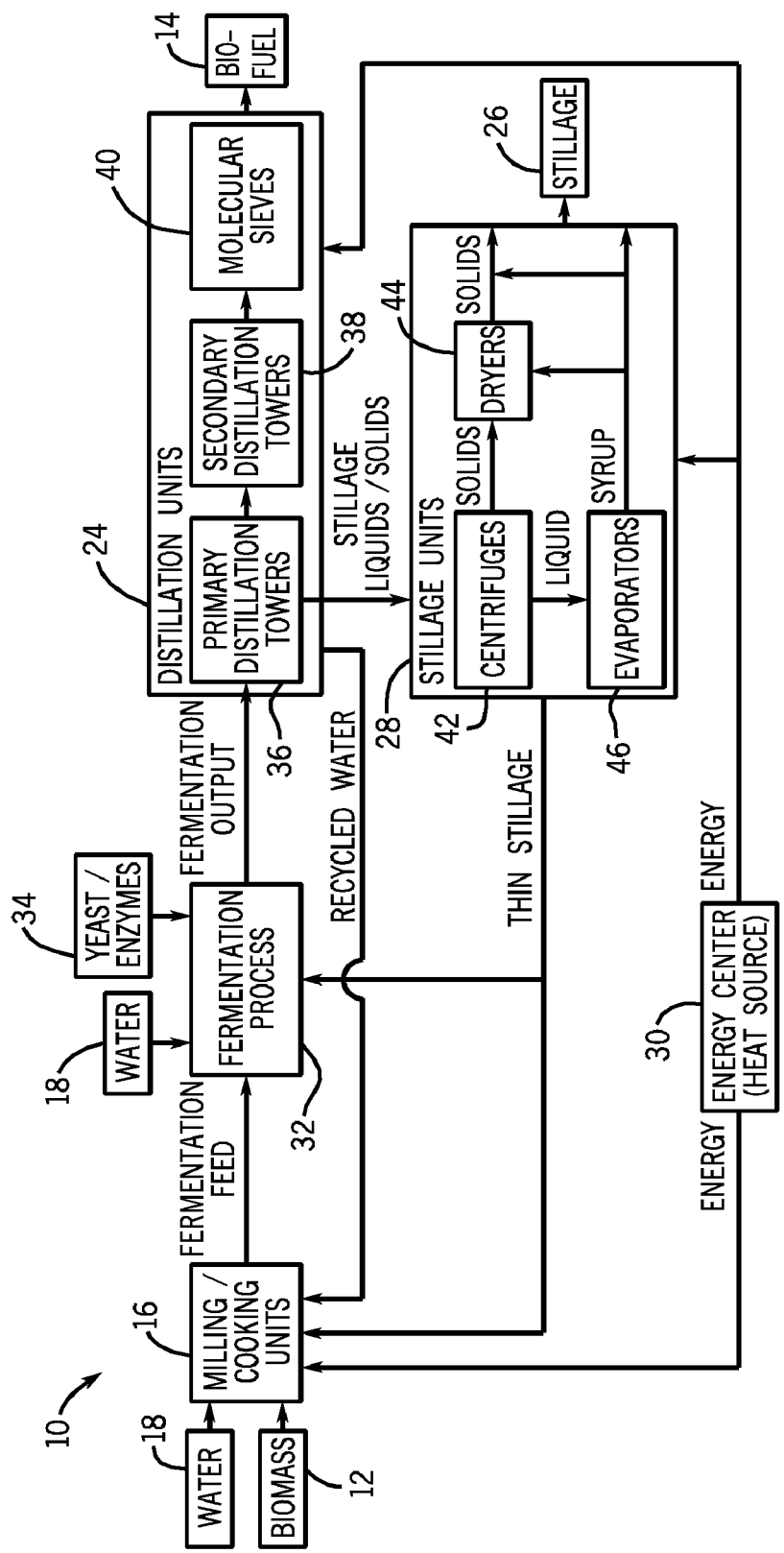
FIG. 2 is a more detailed process flow diagram of sub-processes of an exemplary production plant.

FIG. 2 is a more detailed process flow diagram of sub-processes of an exemplary biofuel production plant 10. It should be noted that the particular components, processes and sub-processes shown are merely meant to be exemplary and are not intended to be limiting. The milling and cooking units 16 may receive water 18, biomass 12, energy (electrical and/or thermal), recycled water, and/or recycled thin stillage, mill the biomass, cook the mixture, and output a biomass slurry (referred to as fermentation feed) to the fermentation process 32, which may include the fermentation vats 20 and beer wells 22 shown in FIG. 1. The fermentation process 32 may receive the biomass slurry, water 18, yeast and enzymes 34, and recycled thin stillage, ferment the mixture, and output fermentation products to the distillation units 24. The distillation units 24 may receive the fermentation products, remove water and stillage (liquid and solid stillage) from the fermentation products in a one- to three-step process (e.g., primary distillation towers 36, secondary distillation towers 38, and/or molecular sieves (dryers) 40), recycle water removed from the fermentation products to the milling and cooking units 16, output the liquid and solid stillage to the stillage processing units 28, and output biofuel 14. The stillage processing units 28 may receive the liquid and solid stillage, process the liquid and solid stillage (utilizing one or more of centrifuge dryers 42, other dryers 44, and/or evaporators 46) to produce and output various stillage 26, and recycle thin stillage liquid to the fermentation process 32 and the milling and cooking units 16. As in FIG. 1 above, the energy center 30 may provide electric power and heat (steam) to the various sub-processes as shown in FIG. 2.

The distillation units 24, which may include primary and secondary distillation towers 36 and 38, may receive the output of the fermentation process 32 (a mixture of biofuel, stillage, and water) and may separate the biofuel 14 from the water and stillage. Stillage may be removed from the primary distillation towers 36 and sent to the stillage processing units 28. Energy may be provided to the distillation units 24 from the energy center 30 and may be primarily used by one or more primary distillation towers 36. The energy may typically be delivered to the primary distillation towers 36 in the form of a steam flow through heat exchangers (not shown), but in some embodiments the steam flow may be added directly to the primary distillation towers 36. Energy may also be recycled to the distillation units 24 from other process flows or provided by other heat sources as needed or desired. The flashed overhead vapor from the primary distillation towers 36 may be transferred to one or more secondary distillation towers 38 (also referred to as the rectifier and side stripper columns). In the secondary distillation towers 38, energy may be provided by heat exchangers utilizing steam and/or heat recovery from other processes, such as the milling and cooking units 16 and/or the stillage processing units 28 utilizing energy recovery streams. The overhead vapor from the primary distillation towers 36 may be a high-purity biofuel (such as an ethanol/water mixture) which may be distilled close to its azeotropic point, but generally below fuel specification requirements. The bottom product stream of the secondary distillation towers 38 may be primarily condensed water. This condensed water may be recycled back to the milling and cooking units 16.

The overhead vapor from the primary distillation towers 36 and the secondary distillation towers 38 may be routed to inventory tanks (not shown) which may be used as surge reservoirs to regulate the feed flow rates between the distillation units and the one or more dehydration units. The dehydration units may be molecular sieve units 40 or other downstream dehydration processing units (e.g., extractive distillation). Molecular sieve units 40 may include an energy-efficient process unit which operates in gas phase using a dehydration process known as pressure swing adsorption (PSA). If the biofuel is ethanol, it may be dehydrated in either the liquid or gas phase. In certain embodiments, molecular sieve units 40 may absorb water in the biofuel vapor such that the resulting biofuel 14 may have only a trace amount of water. When the molecular sieve units 40 become saturated with water, they may be taken offline, replaced with a parallel regenerated unit, and then placed back online. The offline units may be regenerated under conditions that release moisture and allow the units to dry and be ready for future online use. PSA regeneration units may be adjusted to affect the efficiency and capacity of the molecular sieve units 40. The produced biofuel 14 may then be sent to final storage in product inventory tanks (not shown) and/or directed toward additional processing units.

Equipment for processing stillage may include one or more centrifuges 42, one or more evaporators 46, and zero, one, or more dryers 44. The one or more centrifuges 42 may receive a stillage feed (a mixture of liquid and solid stillage) from the bottom outputs of the primary distillation towers 36. The stillage feed from the primary distillation towers 36 may be routed to inventory tanks (not shown) which may be used as surge reservoirs to regulate the stillage feed flow rates between the primary distillation towers 36 and the centrifuges 42. The one or more centrifuges 42 may separate liquids from the stillage feed, output the thin stillage liquids, and output the remaining solids (dewatered stillage, also referred to as wet cake). The solids (including moisture and non-fermentable solids) may be sent to the dryers 44. Part of the thin stillage liquids may be recycled back to the fermentation process 32 and/or the milling and cooking units 16 and the balance may be sent to the one or more evaporators 46 to evaporate moisture from the liquids to form concentrated syrup. The syrup may be sent to a syrup inventory unit (not shown) before being combined with the dewatered stillage in the dryers 44, combined with the dried stillage output from the dryers 44, and/or sold as a stand-alone product. The stillage sub-process equipment may also include various heaters (not shown) and combustors (not shown) for the destruction of volatile organic compounds in the vapors from the drying stillage in the one or more evaporators 46 or dryers 44.

One or more of the processes described above may be managed and controlled via model predictive control utilizing a dynamic multivariate predictive model that may be incorporated as a process model in a dynamic predictive model-based controller. Model predictive control of sub-processes in a biofuel production process is described in greater detail below. In particular, various systems and methods are provided for using model predictive control to improve the yield, throughput, energy efficiency, and so forth of biofuel sub-processes in accordance with specified objectives. These objectives may be set and various portions of the processes controlled continuously to provide real-time control of the production process. The control actions may be subject to or limited by plant and external constraints.

Each of the illustrated sub-processes may operate within the larger biofuel production process to convert biomass 12 to biofuel 14 and possibly one or more co-products. Thus, the biofuel production plant 10 may typically include four general plant sections: milling/cooking, fermentation, distillation/sieves, and stillage processing. Each of these sub-processes may be at least partially dependent upon operation of one or more of the other sub-processes. Moreover, operating conditions that may be optimal for one sub-process may entail or cause inefficiencies in one or more of the other sub-processes. Thus, a plant bottleneck, meaning a local limitation that limits or restricts a global process, may occur in any of the above four sub-processes, thus limiting the overall operation of the biofuel production plant 10.

Thus, an operating challenge for biofuel production is to manage the various sub-processes, and possibly the entire system or process, to automatically respond to a constraint or disruption in the production system or process. As described in greater detail below, integrated model predictive control may be used to manage the biofuel production process in a substantially optimal manner, balancing various, and possibly competing, objectives of the sub-processes to approach, meet, and/or maintain objectives for the overall process. More specifically, the disclosed embodiments of model predictive control may be used to manage the distribution of whole stillage through parallel distribution paths of centrifuges 42 and dryers 44 in the stillage separation and drying sub-processes.

The control of these sub-processes may be performed manually, e.g., based on decisions of a human operator, or may only be locally automated, e.g., via proportional-integral-derivative (PID) inventory controls of fermentation inventory and fermentation feed inventory. However, given the complexity of the relationships among the many factors or variables, such manual control generally results in significant inefficiencies, sub-optimal yields, etc.

Figure 3:
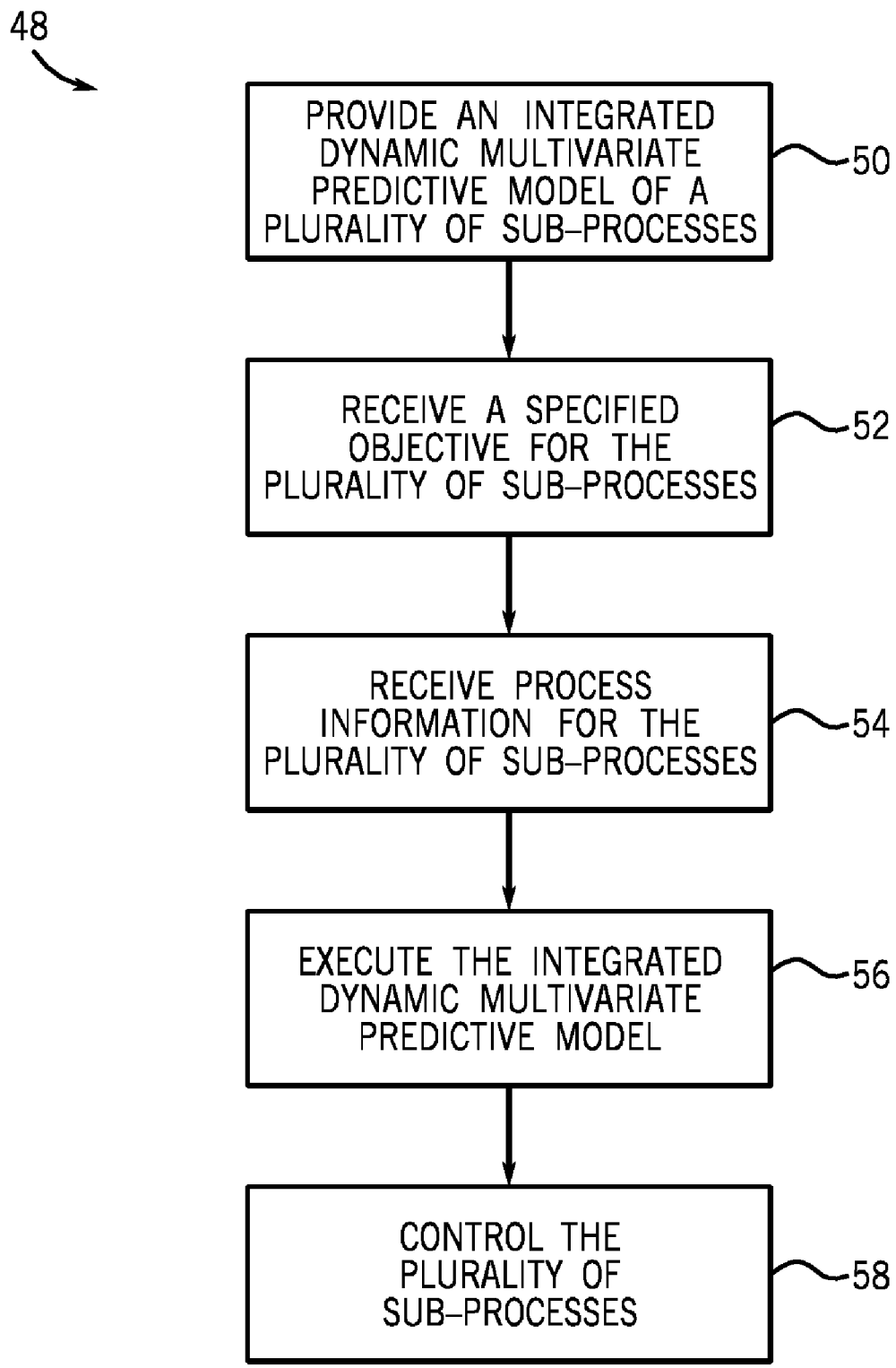
FIG. 3 is a flowchart of an exemplary method for integrated model predictive control of a production process.

FIG. 3 is a flowchart of an exemplary method 48 for such integrated model predictive control of a biofuel production process. More specifically, embodiments of the method 48 may apply model predictive control techniques to manage multiple sub-processes of the biofuel production process in an integrated manner. Note that in various embodiments, many of the method steps may be performed concurrently, in a different order than shown, or may be omitted. Additional method steps may also be performed.

In step 50, an integrated dynamic multivariate predictive model representing a plurality of sub-processes of the biofuel production process may be provided. In other words, a model may be provided that specifies or represents relationships between attributes or variables related to the sub-processes, including relationships between inputs to the sub-processes and resulting outputs of the sub-processes.

The model may be of any of a variety of types. For example, the model may be linear or nonlinear, although for most complex processes, a nonlinear model may be preferred. Other model types contemplated include fundamental or analytical models (i.e., functional physics-based models), empirical models (such as neural networks or support vector machines), rule-based models, statistical models, standard model predictive control models (i.e., fitted models generated by functional fit of data), or hybrid models using any combination of the above models.

The integrated dynamic multivariate predictive model may include a set of mathematical relationships that includes steady state relationships and may also include the time lag relationship for each parameter change to be realized in the output. A great variety of dynamic relationships may be possible and each relationship between variables may characterize or capture how one variable may affect another and also how fast the effects may occur or how soon an effect may be observed at another location.

The integrated dynamic multivariate predictive model may be created from a combination of relationships based on available data such as fundamental dynamic and gain relationships, available plant historic process data, and supplementary plant testing on variables that may not be identified from the two previous steps. Models may be customized to the plant layout and design, critical inventories, plant constraints and measurements, and controllers available to manage variables. Moreover, in some embodiments, external factors, such as economic or regulatory factors, may be included or represented in the model.

An important characteristic of the integrated dynamic multivariate predictive model may be to identify when a control variable changes as a result of a change in one or more manipulated variables. In other words, the model may identify the time-response (e.g., time lag) of one or more attributes of a sub-process with respect to changes in manipulated variables. For example, once a controller adjusts pump speeds, there may be a certain time-dependent response before observing an effect at a tank being filled. This time-dependent response may be unique for each independent controller. For instance, flow rates may vary because of differences in system variables (e.g., piping lengths, tank volumes, and so forth) between the control actuator and sensor and the pump location.

With respect to the stillage processing sub-processes discussed above, stillage feed storage tank levels and individual feeds to the centrifuges 42 may be managed through calculations of the integrated dynamic multivariate predictive model. However, there may be other process disturbances that may remain unmeasured. For example, a situation may occur where a tank level starts to rise out of balance with filling demand (e.g., because of manual plant changes such as scheduled equipment cleaning that involves draining and/or filling one or more specific tanks). In this situation, the integrated dynamic multivariate predictive model may be made aware of the imbalance so that corrective actions may be made gradually to avoid dramatic or critical consequences. This may, for instance, be an issue for many of the tanks that have both batch and continuous plant operations in sequence. Specific tanks may be used to provide storage capacity to facilitate balancing and avoid continuous out-of-control operations after every batch action. Because batch vessels may drain rapidly, specific tank levels may be difficult to maintain in automatic level control. Thus, real-time receipt of current vessel and material balance information (flows and levels) may provide an update on current equipment status and the execution of the integrated dynamic multivariate predictive model may enable projections to be made to avoid both emptying/over-filling vessels and large emergency flow moves to correct imbalances.

In certain embodiments, the integrated dynamic multivariate predictive model may include inferential models (also referred to as property approximators or virtual online analyzers (VOAs)). An inferential model may be a computer-based model which calculates inferred quality properties from one or more inputs of other measured properties (e.g., process stream or process unit temperatures, flows, pressures, concentrations, levels, and so forth). In certain embodiments, the integrated dynamic multivariate predictive model may be subdivided into different portions and stored in a plurality of memories. The memories may be situated in different locations of the biofuel production plant 10. The controller may communicate with the memories utilizing a communication system.

In certain embodiments, the integrated dynamic multivariate predictive model may receive measurements of one or more variables including, but not limited to, one or more of stillage feed rates to the centrifuges 42; flow distribution of stillage between centrifuges 42; recycle backset percentage to the fermentation sub-process 32; liquid inventories of whole stillage, thin stillage, and/or syrup; evaporator syrup percent solids concentration measured by an instrument such as an online density meter or provided by an approximator; heating requirements in the primary distillation towers 36; percent moisture concentration of stillage solid product from the dryers 44, and so forth. The one or more measured variables may include manipulated variables and control variables of the stillage processing sub-processes, and the model-generated target values for the one or more variables may include a target value for each of the one or more manipulated variables.

The integrated dynamic multivariate predictive model may also include at least one control variable that is a control variable, which is a function of at least one manipulated variable of the stillage separation process and/or a function of at least one manipulated variable of the stillage evaporation and/or drying process. For example, the primary distillation towers 36 may be controlled with a separation index and this variable may be a function of distillation feed rate MV and evaporation steam MV in one process design.

In step 52, a specified objective for the plurality of sub-processes may be received. The objective may specify a desired behavior or outcome of the biofuel production process. In certain embodiments, the objective may be somewhat complex or compound. For example, the objective may include a global objective and a plurality of sub-objectives directed to at least a subset of the plurality of sub-processes. In other words, the specified objective may include an overall objective for the biofuel production process, e.g., maximize throughput, efficiency, and so forth, and may also include various subsidiary objectives related specifically to the respective sub-processes. In addition, the sub-objectives may be mutually exclusive or competitive with respect to each other and/or with respect to the global objective.

Exemplary objectives may include, but are not limited to, one or more operator specified objectives, one or more predictive model specified objectives, one or more programmable objectives, one or more target feed rates, one or more cost objectives, one or more quality objectives, one or more equipment maintenance objectives, one or more equipment repair objectives, one or more equipment replacement objectives, one or more economic objectives, one or more target throughputs for the biofuel production process, one or more objectives in response to emergency occurrences, one or more dynamic changes in materials inventory information, one or more dynamic changes in available process energy constraints, or one or more dynamic changes in one or more constraints on the biofuel production process, and so forth.

With respect to the stillage processing sub-processes, the objectives may be specified by a human operator and/or a program. In some embodiments, the objectives may include one or more sub-objectives. The sub-objectives may include one or more of heating load of primary distillation towers 36), rate of loss of biofuel into the stillage feed output from the primary distillation towers 36, combined stillage feed rate to centrifuges 42, individual feed rates to each centrifuge 42, flow rate and inventory of non-fermentable solids output, and flow rate and inventory of stillage liquids recycled and output, water content in one or more stillage output products, and purity specification of each stillage output products. In particular, in certain embodiments, a specific objective may include the determination of optimal distribution of stillage flow rates between parallel paths of centrifuges 42 and dryers 44 in the stillage separation and drying sub-processes.

In step 54, process information related to the plurality of sub-processes may be received from the biofuel production process. This process information may be any type of process information, including state or condition information measured by sensors (e.g., temperatures, pressures, real-time measurements of the biofuel in the fermentation system, and so forth), computed algorithmically, inferred from models (i.e., inferential models), taken from lab values, entered by operators, and so forth. The process information may further include equipment settings, flow rates, material properties (e.g. densities), content profiles, purity levels, ambient conditions (e.g., time of day, temperature, pressure, humidity, and so forth), economic or market conditions (e.g., cost of materials or product), and so forth. In other words, the process information may include any information that affects or influences any part of the biofuel production process.

More specifically, the process information may include measurements of one or more control variables and one or more manipulated variables related to the stillage sub-process and one or more variables of other processes that may impact the stillage sub-process, as well as information from inferential models, laboratory results, and so forth. The measured variables may include any of stillage feed rates from distillation units 24; inventories of stillage in stillage feed holding tanks; limits of stillage feed holding tanks; stillage feed rates to each centrifuge 42; heat input to the dryers 44; output flow rate of liquid stillage; output flow rate of solid stillage; the water content of the stillage from each centrifuge 42; pump speed, valve position, or other controller output within the stillage sub-process; stillage output product composition from one or more dryers 44; water content of the stillage sub-process products; purity specification of one or more stillage output products; and/or the inventory of one or more stillage output products, among others.

In step 56, the integrated dynamic multivariate predictive model may be executed in accordance with the objective using the received process information as input, thereby generating model output comprising target values of one or more controlled variables related to one or more of the plurality of sub-processes in accordance with the objective. In other words, the model may be executed to determine target values for manipulated variables for one or more of the sub-processes that may be used to control the sub-processes in such a way as to attempt to meet the specified objective.

For example, in an embodiment where the objective is to optimize the distribution of flow rates for the sub-process, the model may determine various target values (e.g., sub-process material input flows, temperatures, pressures, and so forth) that may operate to optimize the distribution of flow rates. As another example, in an embodiment where the objective is to minimize energy usage for a sub-process, the model may determine target values that may operate to minimize energy usage for the sub-process, possibly at the expense of total output. In a further example, the objective may be to maximize profit for the entire biofuel production process, where optimizing the distribution of flow rates and minimizing energy usage may be two, possibly competing, sub-objectives, e.g., included in the objective.

It should be noted that as used herein, the terms "maximum," "minimum," and "optimum," may refer respectively to "substantially maximum," "substantially minimum," and "substantially optimum," where "substantially" indicates a value that is within some acceptable tolerance of the theoretical extremum, optimum, or target value. For example, in one embodiment, "substantially" may indicate a value within 10% of the theoretical value. In another embodiment, "substantially" may indicate a value within 5% of the theoretical value. In a further embodiment, "substantially" may indicate a value within 2% of the theoretical value. In yet another embodiment, "substantially" may indicate a value within 1% of the theoretical value. In other words, in all actual cases (non-theoretical), there are physical limitations of the final and intermediate control element, dynamic limitations to the acceptable time frequency for stable control, or fundamental limitations based on currently understood chemical and physical relationships. Within these limitations, the control system will generally attempt to achieve optimum operation, i.e., operate at a targeted value or constraint (maximum or minimum) as closely as possible.

In certain embodiments, the integrated dynamic multivariate predictive model may be executed by a dynamic predictive model-based controller to generate one or more target values in accordance with a specified objective. The target values may correspond to various manipulated variables including, but not limited to whole stillage feed rates and inventory; stillage distribution balance through the centrifuges 42; thin stillage flow rates and inventories including thin stillage recycled back to the fermentation units, and/or thin stillage sent to the evaporators 46 to form a concentrate syrup; percent solids in the concentrate syrup; syrup inventories including syrup combined with partially dried solids in the dryers 44, syrup added to the solids from the dryers 44, syrup sold as a stand-alone product, and so forth; evaporator heating media and draw flow rates; heating requirements in the primary distillation towers 36 (to prevent loss of product alcohol to the stillage process); and/or percent moisture concentration of stillage solid product from the dryers 44, among others. The controller may be configured to generate a plurality of target values for manipulated variables simultaneously.

In step 58, the plurality of sub-processes of the biofuel production process may be controlled in accordance with the target values and the objective. In other words, a controller (or a plurality of controllers) may modulate or otherwise control various operational aspects of the sub-processes in accordance with the target values of the manipulated variables. In some embodiments, the target values may simply be used as set points by the controller. In other words, the controller may set respective inputs of the various sub-processes to the respective target values. For example, controlling the plurality of sub-processes of the biofuel production process in accordance with the target values and the objective may include operating one or more controllers to control one or more of the following: one or more material feed rates, one or more water flows, one or more molecular sieve regenerations, one or more heat sources, and so forth.

Steps 52, 54, 56, and 58 of the method 48 may be performed a plurality of times in an iterative manner to operate the biofuel production process in a substantially optimal fashion. In other words, the method 48 described above may be performed substantially continuously, such as at a specified frequency, providing control of the biofuel production process in substantially real time to optimize the biofuel production process with respect to the specified objective.

In embodiments where multiple objectives may be provided, possibly at odds with one another, an optimizer may be used to balance the various sub-objectives in attempting to meet the global objective. In other words, an optimizer may be used to determine how to compromise with respect to the various sub-objectives in attempting to achieve the global objective. Thus, in certain embodiments, executing the integrated dynamic multivariate predictive model may include an optimizer executing the integrated dynamic multivariate predictive model to generate the model output. The generated model output may include the target values of one or more variables related to one or more of the plurality of sub-processes in accordance with the global objective and the plurality of sub-objectives. In certain embodiments, the optimizer may execute the integrated dynamic multivariate predictive model a plurality of times in an iterative manner. For example, the optimizer may repeatedly execute the model using various inputs and compare the resulting outputs to the specified objective (including the sub-objectives), thereby searching the solution space for input configurations that optimize the outcome, e.g., that allow the global objective to be met or at least approached, while minimizing the compromises made with respect to the various sub-objectives.

In certain embodiments, the method 48 may further include receiving constraint information specifying one or more constraints, such as limitations on one or more aspects or variables of the biofuel production process. The optimizer may execute the integrated dynamic multivariate predictive model in accordance with the objective using the received process information and the one or more constraints as input, thereby generating the model output in accordance with the objective and subject to the one or more constraints. The one or more constraints may include any such limitation on the biofuel production process including, but not limited to, one or more of: batch constraints (e.g., fermentation time), water constraints, feed constraints, equipment constraints, capacity constraints, temperature constraints, pressure constraints, energy constraints, market constraints, economic constraints, environmental constraints, legal constraints, operator-imposed constraints, and so forth. Furthermore, examples of equipment constraints may include, but are not limited to, one or more of: operating limits for pumps, operational status of pumps, tank capacities, operating limits for tank pressures, operational status of tanks, operating limits for valve pressures, operating limits for valve temperatures, operating limits for pipe pressures, operating limits for energy provision, operating limits for molecular sieves, and so forth. Moreover, in certain embodiments, the constraint information may include dynamic constraint information. In other words, some of the constraints may change dynamically over time. Therefore, the method 48 may automatically adjust operations taking into account these changing constraints.

In certain embodiments, the system may derive its measurements or process information from the process instruments or sensors, inferential models, real-time measurements of the biofuel in the fermentation system, and/or lab values, and execute linear or non-linear dynamic prediction models to solve an overall optimization objective which may typically be an economic objective function subject to dynamic constraints of the plant processes. The system may then execute the integrated dynamic multivariate predictive model, controller, and optimizer in accordance with the objective, e.g., the optimization function. For instance, the system may optimize the distribution of stillage flow rates through parallel paths of centrifuges and dryers in the stillage separation and drying sub-processes.

Figure 4:
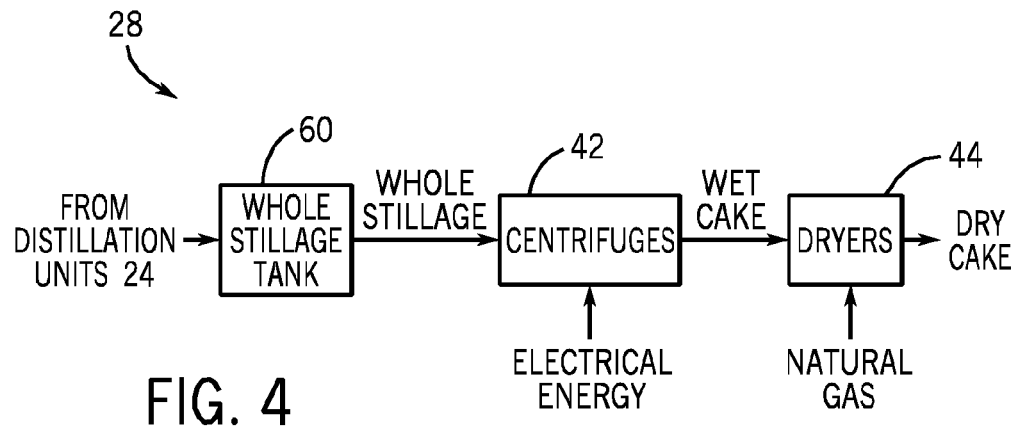
FIG. 4 is a process flow diagram of exemplary stillage separation and drying sub-processes as performed by the components of the stillage processing units illustrated in FIG. 2.

As described above, stillage feed from the distillation units 24 may be routed to the stillage processing units 28, which may include one or more centrifuges 42 and zero, one, or more dryers 44, among other equipment. In general, the centrifuges 42 and dryers 44 may separate the stillage feed (a mixture of liquid and solid stillage) into stillage liquids and stillage solids. FIG. 4 is a process flow diagram of exemplary stillage separation and drying sub-processes as performed by the components of the stillage processing units 28 illustrated in FIG. 2. As shown in FIG. 4, the stillage feed (i.e., whole stillage) may be sent as an output from the distillation units 24 to the whole stillage tanks 60. The whole stillage tanks 60 may function as surge reservoirs to regulate the stillage feed rates from the distillation units 24 to the centrifuges 42.

The centrifuges 42 and dryers 44 perform slightly different functions as part of the stillage separation and drying sub-processes. The centrifuges 42 may use electrical energy as an energy source and may separate stillage liquids from the whole stillage received from the whole stillage tanks 60. Therefore, the output from the centrifuges 42 may include the thin stillage liquids and the remaining de-watered stillage solids (i.e., wet cake). Part of the thin stillage liquids may be recycled back into the fermentation process 32 and/or the milling and cooking units 16, illustrated in FIG. 2. In addition, some of the thin stillage liquids may be sent to one or more evaporators 46, also illustrated in FIG. 2, where moisture may be evaporated from the thin stillage liquids to create syrup. The wet cake generated by the centrifuges 42 may be sent to the dryers 44. The dryers 44 may use natural gas as an energy source and may further dry the wet cake to create dry cake, otherwise known as cattle feed.

Therefore, the centrifuges 42 may separate water to the extent that the wet cake may contain approximately 60% moisture and 40% solids. Then, the dryers 44 may further dry the wet cake to a point where the dry cake may contain approximately 9% moisture, with the remainder being solids. Since the centrifuges 42 and the dryers 44 may perform these functions in a step-wise, complementary fashion, the centrifuges 42 and dryers 44 may often be used together as pairs. When plants expand, multiple parallel paths may be used with each parallel path including centrifuges 42 and dryers 44. This type of expansion enables increased throughput without the need for re-sizing or overloading existing equipment.

Figure 5:
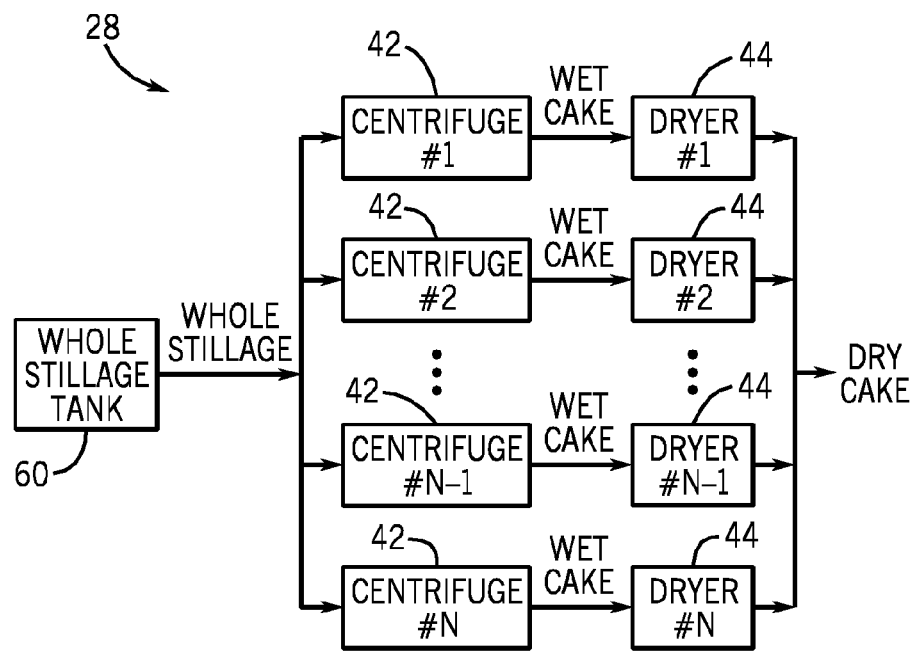
FIG. 5 is a process flow diagram of exemplary parallel paths of centrifuges and dryers which may perform the separation and drying sub-processes of FIG. 4.

For example, FIG. 5 is a process flow diagram of exemplary parallel paths of centrifuges 42 and dryers 44 which may perform the separation and drying sub-processes of FIG. 4. As shown, whole stillage from the whole stillage tanks 60 may be directed through multiple parallel paths of centrifuges 42 and dryers 44. In particular, in the illustrated embodiment, N parallel paths are utilized with each of the N parallel paths including one centrifuge 42 and one dryer 44. However, although described herein as including only one centrifuge 42 and one dryer 44, each parallel path may, in fact, contain one or more centrifuges 42 and zero, one, or more dryers 44.

In addition, although depicted in FIG. 5 as identical units, the centrifuges 42 and dryers 44 in the multiple parallel paths may be characterized by different performance profiles. For example, efficiencies between the units may vary, such as the older dryers 44 being more efficient than newer dryers 44. In addition, the centrifuges 42 and dryers 44 of certain parallel paths may be sized differently than those in other parallel paths. Furthermore, operation of the centrifuges 42 and dryers 44 may be varied by manipulating input variables of the respective units. For example, the torque or feed rate of the centrifuges 42 and the natural gas flow rate of the dryers 44 may be varied, among other variables.

Due at least in part to these varying operational and performance characteristics, the flow of whole stillage may be varied between the multiple parallel paths. One method of distributing the whole stillage between the parallel paths may be to simply distribute the whole stillage proportionally between the multiple paths. For instance, if five parallel paths are used, 20% of the whole stillage may be directed through each path. However, this type of control may not adequately consider the varying operational and performance characteristics of the centrifuges 42 and dryers 44, discussed above. Therefore, a more robust approach to distributing the whole stillage between the multiple parallel paths may enable operators of the biofuel production system 10 to more efficiently utilize the centrifuges 42 and dryers 44 as part of the separation and drying sub-processes. In particular, the costs associated with the separation and drying sub-processes may be minimized by more efficiently distributing the whole stillage between the parallel paths.

Figure 6:
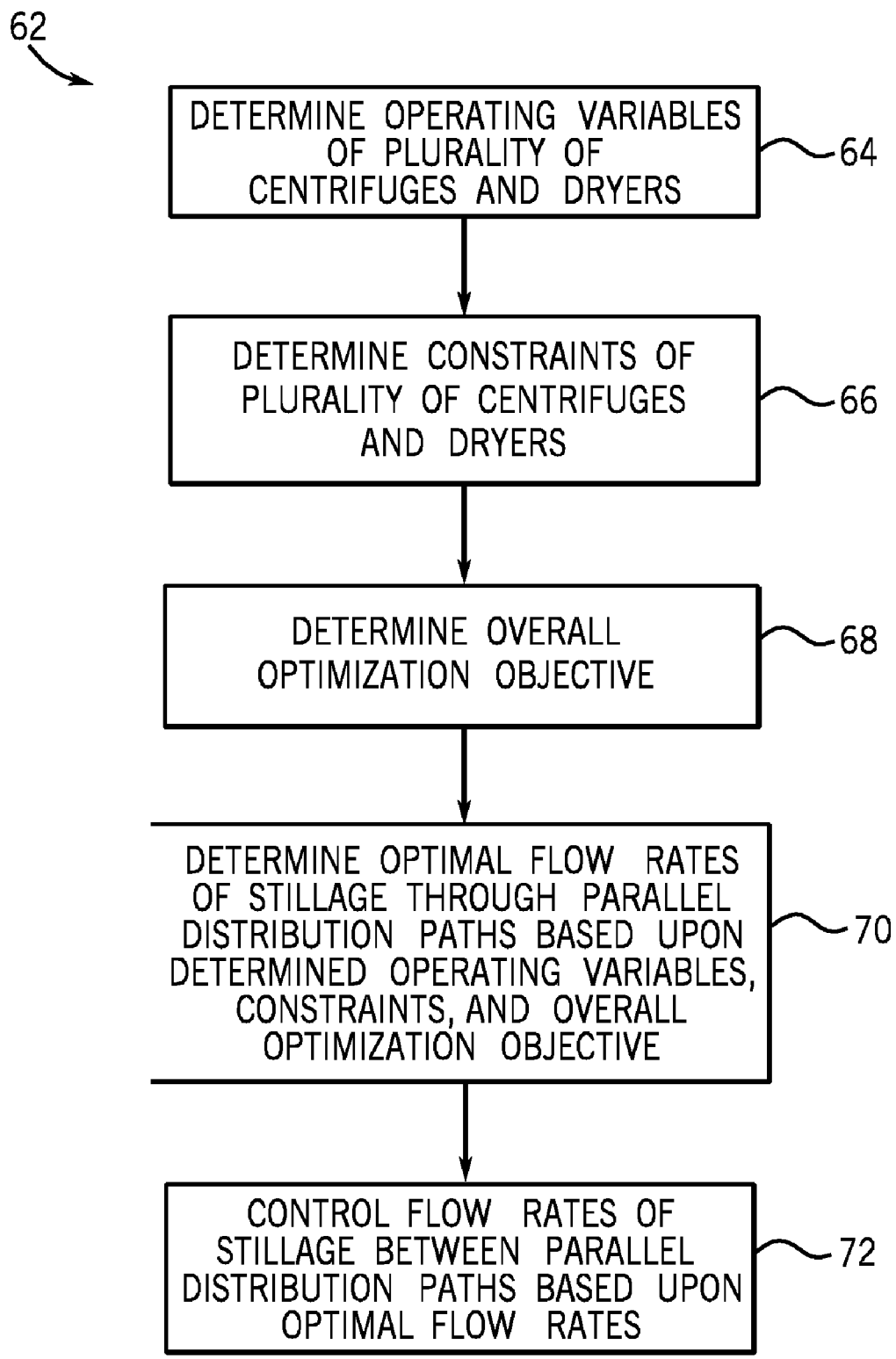
FIG. 6 is a flow chart of an exemplary method for controlling the distribution of whole stillage through the centrifuges and dryers of FIG. 5.

Using the model predictive control techniques discussed in greater detail above, it may be possible to monitor, control, and optimize the sub-processes (in particular, the stillage separation and drying sub-processes) of the biofuel production process in order to implement optimized decisions regarding the distribution of whole stillage through multiple parallel paths of centrifuges 42 and dryers 44. For instance, FIG. 6 is a flow chart of an exemplary method 62 for controlling the distribution of whole stillage through the centrifuges 42 and dryers 44 of FIG. 5. The method 62 may be integrated into the model predictive control method 48 of FIG. 3 above. Indeed, the method 62 may be one exemplary embodiment of the predictive model techniques discussed above.

In step 64, operating variables of a plurality of centrifuges 42 and dryers 44 may be determined. As described above, each of the plurality of centrifuges 42 and dryers 44 may be located within parallel distribution paths. The determined operating variables of the centrifuges 42 and dryers 44 may be any of the variables described above for the centrifuges 42 and dryers 44. Moreover, the determination of the operating variables for the centrifuges 42 and dryers 44 may involve several different techniques. For instance, the operating variables of the centrifuges 42 and dryers 44 may be determined by process instruments. However, certain operating variables of the centrifuges 42 and dryers 44 may not be easily measured. Therefore, proxy values may be determined, for instance, based on inferential models and external calculations. For example, while certain measurements may easily be collected for the dryers 44, certain measurements for the centrifuges 42 may prove somewhat more problematic. Therefore, inferential models using, for instance, energy and mass balance calculations may be used to infer certain operating variables of the centrifuges 42 and dryers 44 whenever reliable and easily-accessible measurements are unavailable.

In addition to operating variables of the centrifuges 42 and dryers 44, operating variables of other equipment may be determined as well. For instance, operating variables of other stillage processing units 28, such as the evaporators 46, may be determined. Moreover, operating variables of equipment in other processes (e.g. the milling and cooking units 16, the fermentation process 32, the distillation units 24, and so forth) throughout the biofuel production plant 10 may be determined. All of these operating variables may be determined using the various techniques described above. Once determined in step 64, the operating variables may be used in step 70 of the method 62.

In step 66, constraints of the plurality of centrifuges 42 and dryers 44 may be determined. These constraints may include, but are not limited to, process constraints, energy constraints, equipment constraints, legal constraints, operator-imposed constraints, and so forth. These constraints may be measured and accounted for in step 70 of the method 62.

In step 68, an overall optimization objective may be determined. The overall optimization objective may be any of a number of various objectives. For instance, in certain embodiments, the overall optimization objective may be to reduce energy costs per unit mass of solids dried. In other embodiments, the overall optimization objective may be to achieve a target or maximum throughput through the plurality of centrifuges 42 and dryers 44. In addition, in further embodiments, the overall optimization objective may be to reduce the overall cost of energy per unit mass dried. For example, in some instance, electrical energy costs may be heavily discounted compared to natural gas costs. Therefore, it may be more costly to do more drying in the most efficient centrifuges 42 than a path that is less efficient. In other words, more drying may be achieved through this line before the balance of the product drying is completed within the dryers 44. It should be noted that this list of possible overall optimization objectives is merely exemplary and not intended to be limiting. The overall optimization objective selected may be used in step 70 of the method 62.

In step 70, optimal flow rates of whole stillage through the parallel distribution paths may be determined based upon the operating variables, constraints, and overall optimization objective determined in steps 64, 66, and 68. This determination of optimal flow rates of whole stillage through the parallel distribution paths may take into account the model predictive control and optimization techniques discussed above. For instance, the predictive model controller may be executed to generate model outputs which may be optimized to determine what the optimal flow rates of whole stillage may be through each of the parallel distribution paths of centrifuges 42 and dryers 44.

Then, in step 72, the flow rates of whole stillage between the parallel distribution paths may be controlled based upon the optimal flow rate determinations from step 70. The control of the flow rates of whole stillage between the parallel distribution paths may include manipulation of any number of the process variables described above. For example, the control of the flow rates may include the manipulation of control valves of the parallel distribution paths, among other things.

The steps 64, 66, 68, 70, and 72 of the method 62 may be cyclically repeated during the biofuel production process. In addition, the steps 64, 66, 68, 70, and 72 of the method 62 may be performed sequentially, simultaneously, or in any order relative to one another.

The control systems used to implement the present techniques may be open or closed. Open loop systems are only defined by the inputs and the inherent characteristics of the system or process. In the biofuel production process, the system may be the entire biofuel production plant, one sub-process of the biofuel production plant, such as the milling and cooking units 16, or control of a variable in a process such as the temperature of the milling and cooking units 16. In a closed loop system, the inputs may be adjusted to compensate for changes in the output where, for example, these changes may be a deviation from desired or targeted measurements. A closed loop system may sense a change and provide a feedback signal to a process input. Process units in the biofuel production system may be closed loop systems if they need to be regulated subject to constraints such as product quality, energy costs, process unit capacity, and so forth. Traditional PID controllers and other control systems such as ratio controls, feed-forward controls, and process models may be used to control biofuel production processes. A distributed control system may have many control schemes set up to control the process unit variables at the local control level.

The control systems may include a computer system with one or more processors, and may include or be coupled to at least one memory medium (which may include a plurality of memory media), where the memory medium may store program instructions according to the present techniques. In various embodiments, controllers may be implemented on a single computer system communicatively coupled to the biofuel production plant 10, or may be distributed across two or more computer systems, e.g., that may be situated at more than one location. In this embodiment, the multiple computer systems comprising the controllers may be connected via a bus or communication network.

The automated control system for the biofuel production plant 10 may include one or more computer systems which interact with the biofuel production plant 10 being controlled. The computer systems may represent any of various types of computer systems or networks of computer systems which execute software programs according to various embodiments of the present techniques. The computer systems may store (and execute) software for managing sub-processes in the biofuel production plant 10. The software programs may perform various aspects of modeling, prediction, optimization and/or control of the sub-processes. Thus, the automated control system may implement predictive model control of the sub-processes in the biofuel production plant 10. The system may further provide an environment for making optimal decisions using an optimization solver (i.e., an optimizer) and carrying out those decisions (e.g., to control the plant).

One or more software programs that perform modeling, prediction, optimization and/or control of the biofuel production plant 10 may be included in the computer systems. Thus, the systems may provide an environment for a scheduling process of programmatically retrieving process information relevant to the sub-processes of the biofuel production plant 10, and generating actions to control the sub-processes, and possibly other processes and aspects of the biofuel production plant 10.

The computer systems may preferably include a non-transitory computer readable memory medium on which computer programs according to the present techniques may be stored. The term "non-transitory computer readable memory medium" is intended to include various types of memory or storage, including an installation medium (e.g., a CD-ROM or floppy disks), a computer system memory or random access memory (e.g., DRAM, SRAM, and so forth), or a non-volatile memory such as a magnetic medium (e.g., a hard drive or optical storage). The memory medium may comprise other types of memory as well, or combinations thereof. In addition, the memory medium may be located in a first computer in which the programs are executed, or may be located in a second different computer which connects to the first computer over a network. In the latter instance, the second computer may provide the program instructions to the first computer for execution.

Also, the computer systems may take various forms, including a personal computer system, mainframe computer system, workstation, network appliance, Internet appliance or other device. In general, the term "computer system" may be broadly defined to encompass any device (or collection of devices) having a processor (or processors) which executes instructions from a memory medium. The memory medium (which may include a plurality of memory media) may preferably store one or more software programs for performing various aspects of model predictive control and optimization. A CPU, such as the host CPU, executing code and data from the memory medium may include a means for creating and executing the software programs.

The present techniques have been presented in the context of optimizing the flow rates of whole stillage through parallel distribution paths of centrifuges 42 and dryers 44 in the production of biofuels. However, the present techniques may also be applied to any other systems where a product may be dried and separated from water and other liquids using multiple parallel paths of centrifuges, dryers, evaporators, and so forth. For instance, the separation and drying of agricultural products may be another application where the present techniques may be used.

Therefore, in general, the present techniques may be applied to various applications where coordination of multiple parallel flow paths in a separation and drying process is desired. While the disclosed embodiments have generally be characterized as relating to multiple parallel paths of centrifuges 42 and dryers 44, the present techniques may also be extended to myriad combinations of separation and drying equipment in parallel paths. Indeed, the present techniques may be applied to any systems which are conducive to being modeled using the model predictive control techniques described herein Moreover, systems where optimization of flow rates through multiple parallel paths of separation and drying equipment may prove useful are particularly well-suited for use with the present techniques.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for controlling the distribution of stillage through a plurality of centrifuges and dryers, comprising:
    (a) determining operating variables of the plurality of centrifuges and dryers, wherein the plurality of centrifuges and dryers are located within parallel distribution paths;
    (b) determining constraints of the plurality of centrifuges and dryers;
    (c) determining an overall optimization objective;
    (d) determining optimal flow rates of stillage through the parallel distribution paths based upon the determined operating variables, constraints, and overall optimization objective; and
    (e) controlling the flow rates of stillage between the parallel distribution paths based upon the optimal flow rate determinations.

2. The method of claim 1, comprising determining operating variables of other stillage processing units for use in step (d).

3. The method of claim 1, comprising determining operating variables of milling and cooking units, fermentation process units, distillation units, or a combination thereof, for use in step (d).

4. The method of claim 1, comprising measuring the operating variables using process instruments.

5. The method of claim 1, comprising utilizing inferential models for determining the operating variables.

6. The method of claim 1, wherein the constraints comprise process constraints, energy constraints, equipment constraints, legal constraints, operator-imposed constraints, or a combination thereof.

7. The method of claim 1, wherein the overall optimization objective is to reduce energy costs per unit mass of solids dried.

8. The method of claim 1, wherein the overall optimization objective is to achieve a target or maximum throughput through the plurality of centrifuges and dryers.

9. The method of claim 1, wherein the overall optimization objective is to reduce the overall cost of energy per unit mass dried.

10. The method of claim 1, comprising cyclically repeating steps (a)-(e) during operation.

11. The method of claim 1, wherein steps (a)-(e) are performed sequentially or performed simultaneously.

12. A non-transitory computer readable medium, comprising:
    computer code disposed on the non-transitory computer readable medium, wherein the code comprises instructions for controlling the distribution of stillage through a plurality of centrifuges and dryers, the instructions comprising:
        instructions for determining operating variables of the plurality of centrifuges and dryers, wherein the plurality of centrifuges and dryers are located within parallel distribution paths;
        instructions for determining constraints of the plurality of centrifuges and dryers;
        instructions for determining an overall optimization objective;
        instructions for determining optimal flow rates of stillage through the parallel distribution paths based upon the determined operating variables, constraints, and overall optimization objective; and
        instructions for controlling the flow rates of stillage between the parallel distribution paths based upon the optimal flow rate determinations.

13. The non-transitory computer readable medium of claim 12, wherein the overall optimization objective is to reduce energy costs per unit mass of solids dried.

14. The non-transitory computer readable medium of claim 12, wherein the overall optimization objective is to achieve a target or maximum throughput through the plurality of centrifuges and dryers.

15. The non-transitory computer readable medium of claim 12, wherein the overall optimization objective is to reduce the overall cost of energy per unit mass dried.

16. The non-transitory computer readable medium of claim 12, wherein the instructions are cyclically repeated.

17. A process controller for controlling the distribution of stillage through centrifuges and dryers, comprising:
a computer readable medium comprising computer code disposed on the computer readable medium, wherein the code comprises instructions for controlling the distribution of stillage through a plurality of centrifuges and dryers, the instructions comprising:
instructions for determining operating variables of the plurality of centrifuges and dryers, wherein the plurality of centrifuges and dryers are located within parallel distribution paths;
instructions for determining constraints of the plurality of centrifuges and dryers;
instructions for determining an overall optimization objective;
instructions for determining optimal flow rates of stillage through the parallel distribution paths based upon the determined operating variables, constraints, and overall optimization objective; and
instructions for controlling the flow rates of stillage between the parallel distribution paths based upon the optimal flow rate determinations.

18. The process controller of claim 17, wherein the overall optimization objective is to reduce energy costs per unit mass of solids dried.

19. The process controller of claim 17, wherein the overall optimization objective is to achieve a target or maximum throughput through the plurality of centrifuges and dryers.

20. The process controller of claim 17, wherein the overall optimization objective is to reduce the overall cost of energy per unit mass dried.

* * * * *